US008518387B2

(12) United States Patent
Drovetskaya et al.

(10) Patent No.: US 8,518,387 B2
(45) Date of Patent: Aug. 27, 2013

(54) PERSONAL CARE COMPOSITIONS WITH TERTIARY AMINO MODIFIED CELLULOSE DERIVATIVES

(75) Inventors: Tatiana V. Drovetskaya, Basking Ridge, NJ (US); Emmet M. Partain, Bound Brook, NJ (US)

(73) Assignee: Union Carbide Chemicals & Plastics Technology LLC

( * ) Notice: Subject to any disclaimer, the term of this patent is extended or adjusted under 35 U.S.C. 154(b) by 0 days.

(21) Appl. No.: 12/967,527

(22) Filed: Dec. 14, 2010

(65) Prior Publication Data

US 2011/0142779 A1  Jun. 16, 2011

Related U.S. Application Data

(60) Provisional application No. 61/287,025, filed on Dec. 16, 2009.

(51) Int. Cl.
*A61K 8/73* (2006.01)
*A61Q 5/02* (2006.01)
*A61Q 5/12* (2006.01)

(52) U.S. Cl.
USPC ........................................ 424/70.13; 510/119

(58) Field of Classification Search
USPC ........................................ 424/70.13; 514/119
See application file for complete search history.

(56) References Cited

U.S. PATENT DOCUMENTS

| | | | |
|---|---|---|---|
| 1,777,970 A | 10/1930 | Hartman | |
| 2,623,042 A | 12/1952 | Vaughn | |
| 2,970,140 A | 1/1961 | Hullinger et al. | |
| 3,472,840 A | 10/1969 | Stone et al. | |
| 3,732,073 A | 5/1973 | Rowland et al. | |
| 3,823,133 A | 7/1974 | Hurst et al. | |
| 4,358,587 A | 11/1982 | Brandt et al. | |
| 4,550,161 A | 10/1985 | Felcht et al. | |
| 4,663,159 A | 5/1987 | Brode, II et al. | |
| 2004/0157754 A1* | 8/2004 | Geary et al. | 510/119 |
| 2005/0139130 A1 | 6/2005 | Partain, III et al. | |
| 2007/0136954 A1 | 6/2007 | Penninger et al. | |
| 2009/0283106 A1* | 11/2009 | Torgerson et al. | 132/202 |
| 2009/0318326 A1* | 12/2009 | Lant | 510/320 |

OTHER PUBLICATIONS

Peterson et al.; "Chromatography of Proteins"; Cellulose Ion-Exchange Adsorbents; Feb. 20, 1956; pp. 751-755; vol. 78.
Perrier et al.; "Mono- and Diquaternary Ammonium Cellulose Cottons Prepared in Nonaqueous Media"; Journal of Applied Polymer Science; 1975; pp. 3211-3220; vol. 19; John Wiley & Sons, Inc.
Benerito et al.; "Preparation and Properties of Quaternary Cellulose Anion Exchangers"; Dec. 1965; pp. 1693-1699; vol. 37; No. 13.
Yoo et al.; "Physicochemical Properties and Biological Activites of DEAE-Derivatized Sphingomonas Gellan"; Journal of Agricultural and Food Chemisty; 2005; pp. 6235-6239; vol. 53; American Chemical Society.
Bullock et al.; "Diethylaminoethylcellulose", in Methods in Carbohydrate Chemistry, ed. R. L. Whistler, pp. 409-411; vol. 5; Academic Press, 1965.
Sober et al.; "Fractionation of Serum Protein on Anion-exchange Cellulose", Journal of the American Chemical Society; 1956; pp. 756-763; vol. 78.
"Funny Honey Shampoo & Conditioner", Mintel, Dec. 2009.
"Moisturizing Body Wash with Coca Butter", Mintel, Dec. 2009.
"Angel Shampooing Celeste", Mintel, Aug. 2004.
"Eau Tranquility Bath & Shower Milk", Mintel, Apr. 2004.
"Polyquaternium-10: International Cosmetic Ingredient Dictionary and Handbook", The Cosmetic Toiletry, and Fragrance Association, 2006, vol. 2, p. 1847.
"Polyquaternium-24: International Cosmetic Ingredient Dictionary and Handbook", The Cosmetic, Toiletry, and Fragrance Association, 2006, vol. 2, p. 1849.
"Polyquaternium-67: International Cosmetic Ingredient Dictionary and Handbook", The Cosmetic, Toiletry, and Fragrance Association, 2006, vol. 2, p. 1856.

\* cited by examiner

*Primary Examiner* — Anoop Singh
*Assistant Examiner* — Anna Falkowitz

(57) ABSTRACT

Described are personal care compositions, comprising an aqueous dispersion comprising an ethylene acrylic acid copolymer and a least one cosmetically acceptable surfactant, emollient, or cosmetic active.

17 Claims, No Drawings

PERSONAL CARE COMPOSITIONS WITH TERTIARY AMINO MODIFIED CELLULOSE DERIVATIVES

CROSS-REFERENCE TO RELATED APPLICATION

This application claims benefit of priority from U.S. Provisional Patent Application No. 61/287,025, filed Dec. 16, 2009, which application is incorporated by reference herein in its entirety.

FIELD

The present application relates to personal care compositions.

BACKGROUND

As a matter of background, cellulose is a linear, unbranched polysaccharide composed of anhydroglucose monosaccharide units linked through their 1, 4 positions by the β anomeric configuration. Substitution of the hydroxyl groups (with positions at 2, 3, or 6) will yield cellulose derivatives. Common substitutions include methyl (methylcellulose), ethyl (ethylcellulose), ethoxy (hydroxyethylcellulose), isopropyloxy (hydroxypropylcellulose), and mixtures thereof, such as hydroxypropyl methylcellulose. The theoretical limit of hydroxyl substitution is three. As not every anhydroglucose unit will be substituted identically, the average number of hydroxyl groups substituted per anhydroglucose unit is referred to as the degree of substitution, i.e., as a mean over the whole polymer chain.

Terminal hydroxyl groups of substituents may further be substituted with a quaternary amine to form extremely useful personal care compositions, such as cationic cellulose derivatives (including, for example, polyquaterniums, PQ 10, PQ 24, and PQ 67). Conditioning of hair and/or skin is one of the most desired attributes in a personal care composition, particularly conditioners, shampoos, and body washes, and polyquaterniums are known to provide excellent conditioning benefits. However, polyquaterniums can have some drawbacks.

Heretofore, tertiary amines have not been used in personal care compositions because it was believed that polyquaterniums were superior because they are permanently charged, independent of the pH of their solution.

Given the focus in the art toward developing new conditioning agents with desirable attributes, even modest improvements in performance are of importance.

SUMMARY

In one embodiment, the present invention provides personal care compositions, comprising a tertiary amine substituted cellulose derivative and a least one cosmetically acceptable surfactant, emollient, or cosmetic active.

DETAILED DESCRIPTION

In one embodiment, the present invention provides personal care compositions, comprising a tertiary amine substituted cellulose derivative and a least one cosmetically acceptable surfactant, emollient, or cosmetic active.

"Personal care" relates to compositions to be topically applied to a person (including mouth, ear, and nasal cavities, but not ingested). Examples of personal care compositions include skin care products (e.g., facial cream, moisturizers, leave on and rinse off lotions, sunscreens, foundation, mascara, eye-liner, lipstick, cleansers, and the like) and hair care products (including shampoos, leave on and rinse off conditioners, styling gels and hairsprays). Preferably, the personal care composition is a shampoo, a rinse-off conditioner, a leave-in conditioner, or a body wash. Preferably, the personal care composition is not an emulsion.

"Cosmetically acceptable" refers to ingredients typically used in personal care compositions, and is intended to underscore that materials that are toxic when present in the amounts typically found in personal care compositions are not contemplated as part of the present invention.

In one embodiment, the present invention provides a tertiary amine substituted cellulose derivative having a Formula (I):

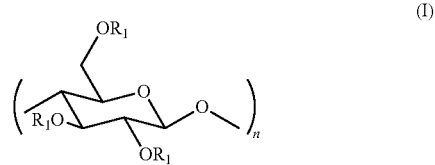

wherein n is an integer sufficient to produce a polymer with a weight-average molecular weight (Mw) in the range of about 50,000 to 2,000,000;

$R_1$ is, independently at each occurrence, H, —$CH_3$, —$CH_2CH_2O$—$R_2$, —$CH_2CH_2O$—$R_2CH_3$, provided that at least one $R_1$ will be other than H; and $R_2$ is, independently at each occurrence, H, $R_3N(R_4)_2$ or it salt, provided that at least one $R_2$ will be $R_3N(R_4)_2$ or its salt, wherein:

$R_3$ is $C_{1-6}$ alkylene or O—$C_{1-6}$ alkylene;

$R_4$ is, independently at each occurrence, $C_{1-6}$ alkyl, or both $R_4$ groups may cooperate along with the nitrogen to which they are attached to form a saturated or unsaturated 5 or 6 member ring.

The term "alkylene" refers to a diradical alkyl group.

Unless specified otherwise, all radicals include optionally substituted embodiments. "Optionally substituted" refers to hydroxyl, alkoxy, carboxy, nitro, amino, amido, halo, or $C_{1-3}$ alkyl.

Accordingly, for example, Formula I specifically contemplates $R_3C_{1-6}$ alkylene as —$CH_2CH(OH)CH_2$— and —$CH_2CH(OH)$—. The $R_3$ portion of Formula I is generally considered a bridge or tether to connect the remainder of the tertiary amine ($N(R_4)_2$ or its salt (i.e., $N^+(R_4)_2H$) to the cellulose ether. Examples of $R_3$ when it is O—$C_{1-6}$ alkylene include —O—$CH_2$—, —O—$CH_2CH_2$—, and —O—$CH_2$—$CH(CH_3)$—.

In a preferred embodiment, $R_1$ is H or —$CH_2CH_2O$—$R_2$, thus the preferred cellulose derivative is hydroxyethylcellulose.

In a preferred embodiment, $R_3$ is —$CH_2CH_2$— or —$CH_2CH(OH)CH_2$—.

In a preferred embodiment, $R_4$ is, independently, $CH_3$ or $CH_2CH_3$.

In one embodiment, the Kjeldahl nitrogen content is from about 0.02% to about 7.5%, preferably about 0.1% to about 5%, most preferably from about 0.2% to about 3%.

In one embodiment, tertiary amine substituted cellulose derivative is present in a range from about 5 wt % to about 40 wt % by weight of the aqueous dispersion, preferably in a range from about 15 wt % to about 25 wt %.

Non-limiting examples of the hydroxyethylcellulose embodiment of the present invention include N,N-diethylaminoethyl hydroxyethylcellulose, N,N-dimethylaminoethyl hydroxyethylcellulose, N,N-diisopropylaminoethyl hydroxyethylcellulose, N,N-dimethylaminopropyl hydroxyethylcellulose, N-ethyl piperidine hydroxyethylcellulose, N-ethyl morpholine hydroxyethylcellulose, and N-ethyl pyrrolidine hydroxyethylcellulose.

In one embodiment, the present invention provides personal care compositions, comprising a tertiary amine substituted cellulose derivative and a silicone. Silicones include silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. A preferred blend of dimethicone, Laureth-23, and C 12-15 Pareth-3 is commercially available from Dow-Corning under the tradename DOW CORNING 2-1491 Silicone Emulsion, also described as a 60% large particle size non-ionic emulsion of a blend of ultra-high molecular weight polydimethylsiloxane gum and intermediate molecular weight polydimethylsiloxane fluid. Preferably, the silicone is present in a range from about 0.1 wt % to about 5 wt %, preferably from about 0.75 wt % to about 3 wt %, and more preferably from about 1 wt % to about 2 wt %, by weight of the personal care composition.

The surfactant is a cationic, anionic, nonionic, or amphoteric surfactant, or a mixture thereof. In one embodiment, the surfactant is a nonionic/emulsifier surfactant. In one embodiment, the surfactant is a cationic surfactant, preferably behentrimonium chloride. In this embodiment, the surfactant is present in an amount from about 0.1 wt % to about 10 wt % by weight of the composition, preferably from about 0.5 wt % to about 7 wt % by weight of the composition, most preferably from about 1 wt % to about 4 wt % by weight of the composition.

In one embodiment, the surfactant is a detergent surfactant. In this embodiment, the surfactant is present in an amount from about 1 wt % to about 25 wt % by weight of the composition, preferably from about 5 wt % to about 20 wt % by weight of the composition, most preferably from about 7 wt % to about 18 wt % by weight of the composition.

Preferably, the detergent surfactant is an anionic surfactant in combination with an amphoteric surfactant. In one embodiment, the anionic surfactant is ammonium laureth sulfate, ammonium lauryl sulfate, sodium laureth sulfate, or sodium lauryl sulfate. In one embodiment, the anionic surfactant is present in an amount from about 1 wt % to about 25 wt %, preferably from about 5 wt % to about 20 wt %, more preferably from about 7 wt % to about 15 wt %, by weight of the composition.

In one embodiment, the mixture is an anionic surfactant in combination with a second surfactant that is disodium cocoamphodiacetate, decylglucoside, or cocamidopropyl betaine. In one embodiment, the second surfactant is present in an amount from about 1 wt % to about 10 wt %, preferably from about 1 wt % to about 8 wt %, more preferably from about 2 wt % to about 6 wt %, by weight of the composition.

In a preferred embodiment, the surfactant is a mixture of sodium laureth sulfate (such as is commercially available from Cognis as under the tradename STANDAPOL ES) and disodium cocoamphodiacetate (such as is commercially available from Henkel as under the tradename VELVETEX CDC). When the surfactant is a mixture of sodium laureth sulfate and disodium cocoamphodiacetate, the ratio of sodium laureth sulfate to disodium cocoamphodiacetate is in a range from about 9:1 to about 2:1, most preferably about 6:1.

In one embodiment, the composition includes citric acid to adjust the pH.

Other optional ingredients for personal care compositions of the present invention include cosmetically acceptable emollients, sunscreens, surfactants, emulsifiers, preservatives, rheology modifiers, colorants, dyes, preservatives, pH adjustors, propellants, reducing agents, fragrances, foaming agents, tanning agents, depilatory agents, flavors, astringents, antiseptics, deodorants, antiperspirants, insect repellants, bleaches, lighteners, anti-dandruff agents, adhesives, polishes, strengtheners, fillers, barrier materials, or biocides.

In some embodiments, the personal care composition further comprises an optional rheology modifier as a thickener. Examples of thickeners include polymers, for example, modified or unmodified carboxyvinyl polymers, such as the products sold under the names CARBOPOL and PEMULEN (INCI name: Acrylates/$C_{10-30}$ alkyl acrylate crosspolymer; available from Noveon), polyacrylates and polymethacrylates, such as the products sold under the names LUBRAJEL and NORGEL (commercially available from Guardian) or HISPAGEL (commercially available from Hispano Chimica), polyacrylamides, 2-acrylamido-2-methylpropane-sulfonic acid polymers and polymers, which are optionally crosslinked and/or neutralized, for instance the poly(2-acrylamido-2-methylpropane-sulfonic acid) sold by Clariant (INCI name: ammonium polyacryldimethyltauramide), emulsified crosslinked anionic polymers of acrylamide and AMPS, such as those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate polymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, cellulose derivatives, associative polymers, for instance associative polyurethanes, polymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (commercially available from Hüs America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (commercially available from Röhm & Haas).

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (commercially available from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes from the list above can also optionally be used.

Preservatives include alcohols, aldehydes, methylchloroisothiazolinone and methylisothiazolinone, p-hydroxybenzoates, and in particular methylparaben, propylparaben, glutaraldehyde and ethyl alcohol.

The pH adjustors, include inorganic and organic acids and bases and in particular aqueous ammonia, citric acid, phosphoric acid, acetic acid, and sodium hydroxide.

Reducing agents include ammonium thioglycolate, hydroquinone and sodium thioglycolate.

Fragrances can be aldehydes, ketones, or oils obtained by extraction of natural substances or synthetically produced as described above. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

The amount of optional ingredients effective for achieving the desired property provided by such ingredients can be readily determined by one skilled in the art.

In a preferred embodiment, the personal care composition is a shampoo, body wash, or facial cleanser, preferably a shampoo.

In use, the personal care compositions are applied to hair or skin. In one embodiment, applying the present personal care compositions constitute a method of conditioning hair.

EXAMPLES

The following examples are for illustrative purposes only and are not intended to limit the scope of the present invention. All percentages are by weight unless otherwise specified.

Example 1

Personal care compositions of the present invention include the following tertiary amines:

Batch A:

32.28 g (30.00 g contained) of CELLOSIZE® QP-100 MH hydroxyethylcellulose and 180.0 g of isopropyl alcohol are placed in a 500 ml resin kettle (or four-necked round-bottomed flask) fitted with a stirring paddle, a nitrogen inlet, a reflux condenser connected to a mineral oil bubbler, a pressure-equalizing addition funnel, a thermometer, and a rubber serum cap. The slurry is stirred and purged with nitrogen for about an hour.

The addition funnel is charged with a solution of 18.6 g of 2-chloro-N,N-diethylethylamine hydrochloride (a.k.a. N,N-diethylaminoethyl chloride hydrochloride) in 43.4 g of distilled water (mole ratio of amine to cellulose derivative of 0.901). The solution in the addition funnel is added drop-wise to the slurry with stirring over about 15 minutes. After completion of addition, 12.25 g of 50% aqueous sodium hydroxide solution is added drop-wise to the slurry over about 5 minutes. The resulting mixture is heated and held at about 40° C. for about two hours, then cooled to room temperature and neutralized by adding 5.00 g of glacial acetic acid and stirring for about 15 minutes.

The resulting polymer is recovered by vacuum filtration through a Buchner funnel and washed a Waring blender, five times with 500 ml of 5:1 (by volume) acetone/water and twice with 500 ml of pure acetone. The polymer may be glyoxal treated in the last desiccation step (second pure acetone wash) by adding 0.6 g of 40% glyoxal and 0.4 g of glacial acetic acid. The polymer is dried overnight in vacuo at 50° C.

The final product is characterized for volatiles (6.62%) and ash (6.18%, as sodium acetate) using conventional methods. The Brookfield viscosity is measured at 30 rpm (1%, corrected for ash and volatiles) and found to be 2500 cP. The Kjeldahl nitrogen content (corrected for ash and volatiles) is found to be 2.11%.

Batch B:

Prepared as described in Batch A, except using CELLOSIZE AM-103 hydroxyethylcellulose, a lower molecular weight product.

Example 2

Exemplary and comparative personal care clear shampoo compositions contain the components recited in TABLE 1 on a weight/weight basis (wt. %).

TABLE 1

| | Formulation A | Comparative Formation 1 |
|---|---|---|
| STANDAPOL ES-2 sodium laureth sulfate (25.5%) | 60.8 | 60.8 |
| VELVETEX CDC disodium cocoamphodiacetate (38.5%) | 6.9 | 6.9 |
| Batch A | 20 | 0 |
| Polyquaternium 10 | 0 | 20 |
| Citric Acid (10%) | 2.3 | 2.2 |
| GLYDANT DMDM Hydantoin | 0.4 | 0.4 |
| Deionized water | q.s. | q.s. |

Combine Batch A with base surfactants. Slowly heat to about 65° C. while mixing with an overhead stirrer (approximately 500 rpm). Continue stirring until surfactants are in solution. Cool to room temperature. Add 10% citric acid and stir about 10 minutes. Add Glydant preservative and q.s. with water to 100 g. Stir about 15 min at approximately 500 rpm.

Control shampoo (Comparative Formulation 1) is prepared substantially as described above but the tertiary amine is replaced by a conventional cationic cellulose derivatives (PQ-10), which has a substantially similar molecular weight and Kjeldahl nitrogen content, but is a quaternary amine.

Example 3

Compositions substantially according to the protocols of Example 2 were prepared. Pre-washed and pre-hydrated tresses of European single-bleached hair (available from International Hair Importers and Products Inc.) were treated with 0.5 g of these shampoo formulations. The shampoo was worked into the hair for 1 min. and then rinsed off under running tap water at 38° C. at 0.4 gal./min. water flow.

The wet combing peak force (WCPF) was measured by using the load cell of an Instron Tensile Tester. The wet combability of a shampoo formulation was calculated as follows in terms of the wet combing force (WCPF), percent reduction of a hair tress treated with a formulation, as compared to a hair tress treated with a base formulation comprising the same ingredients but no quaternary or tertiary amino group-substituted HEC polymers, and reported in TABLE 2:

TABLE 2

|  | WCPF % reduction (%) |
| --- | --- |
| Formulation A | 70 |
| Comparative Formation 1 | 59 |

The statistically significant results show that inventive Formulation A actually had better conditioning performance (as greater reduction in the wet comb peak force) than the benchmark shampoo. This is particularly surprising as the charged cellulosic derivatives that they contain have substantially similar molecular weight and Kjeldahl nitrogen content, and differ only in the tertiary versus quaternized amine. Since those skilled in the art equate conditioning with charge, one would expect comparable performance at best.

Example 4

Exemplary and comparative personal care 2-in-1 shampoo compositions contain the components recited in TABLE 3 on a weight/weight basis (wt. %).

TABLE 3

|  | Formulation B | Comparative Formulation 2 |
| --- | --- | --- |
| STANDAPOL ES-2 sodium laureth sulfate (25.5%) | 60.8 | 60.8 |
| VELVETEX CDC disodium cocoamphodiacetate (38.5%) | 6.9 | 6.9 |
| Batch A | 16.7 | 0 |
| Polyquaternium 10 | 0 | 16.7 |
| DC 1664 trimethyl-trimethylsilyloxy-silane (50%) | 2.0 | 2.0 |
| LEXEMUL EGDS pearlizing agent | 2.0 | 2.0 |
| Citric Acid (10%) | 2.2 | 2.2 |
| GLYDANT DMDM Hydantoin | 0.4 | 0.4 |
| Deionized water | q.s. | q.s. |

Combine base surfactants. Slowly heat to 74° C. while mixing with an overhead stirrer (approximately 500 rpm). Continue stirring until surfactants are in solution. Add pearlizing agent at approximately 550 rpm, maintaining speed for 15 minutes, then cool slowly to about 35° C. Increase stirrer speed to 750 ppm and add silicone. Stir for about 15 minutes. Slowly add Batch A or PQ-10 (as appropriate) and stir about 30 minutes. Add 10% citric acid and stir about 10 minutes. Add Glydant preservative and q.s. with water to 100 g.

Example 5

Compositions substantially according to the protocols of Example 4 were prepared. Pre-washed and pre-hydrated tresses of European Virgin-Brown (available from International Hair Importers and Products Inc.) were treated with 0.5 g of these shampoo formulations. Twice, the shampoo was worked into the hair for 1 min. and then rinsed off under running tap water at 38° C. at 0.4 gal./min. water flow.

The total amount of silicone deposited on hair treated with Formulation B or Comparative Formulation 2 was measured using atomic absorption spectrophotometry. The silicone was extracted from the hair by a 50/50 (v/v) methyl isobutyl ketone/toluene solution. The silicone content was measured, and then the deposition in micrograms of silicone per gram of hair (i.e., ppm) was calculated and reported in TABLE 4:

TABLE 4

|  | Silicon oil, ppm | Average ppm (Std. Deviation) |
| --- | --- | --- |
| Formulation B | 1300 | 1017.7 (331.3) |
|  | 1100 |  |
|  | 653 |  |
| Comparative Formation 2 | 133 | 156.5 (34.6) |
|  | 132 |  |
|  | 181 |  |

The statistically significant results show that inventive Formulation B had remarkably higher silicon deposition than the benchmark shampoo, which showed conventional deposition. This is particularly surprising as the charged cellulosic derivatives that they contain have substantially similar molecular weight and Kjeldahl nitrogen content, and differ only in the tertiary versus quaternized amine.

In another evaluation, wet hair tresses as above were hung until completely dried, and dry sensory evaluations were conducted. Five expert panelists trained to evaluate the performance of cosmetic products on hair were asked to evaluate comb-ability and feel in the dry stage. Each panelist evaluated a pair of tresses, one tress treated with a composition of the invention versus one treated with a comparative composition. The panelists were asked to pick one tress with superior dry attributes, with results given in TABLE 5:

TABLE 5

|  | Formulation B | Comparative Formulation 2 |
| --- | --- | --- |
| Dry comb | 9/10 | 1/10 |
| Dry feel | 9/10 | 1/10 |

These subjective evaluations were statistically analyzed to identify differences at above 89% confidence level. The results show that inventive Formulation B had superior dry sensory attributes.

Example 6

Exemplary personal care rinse off conditioner compositions of the present invention contain the components recited in TABLE 6 on a weight/weight basis (wt. %).

TABLE 6

|  | Formulation C |
| --- | --- |
| CELLOSIZE PCG-10 Hydroxyethylcellulose | 0.5 |
| LEXEMUL EGDS pearlizing agent | 0.5 |
| Batch B | 0.5 |
| LANNETTE O Cetearyl Alcohol | 2.0 |
| LANNETTE 16 Cetyl Alcohol | 0.5 |
| PROTAMATE 4400DPS PEG-100 Stearate | 1.0 |
| JEEQUAT SDQ-85 Stearalkonium Chloride | 2.0 |
| Citric Acid (10%) | 0.05 |
| GLYDANT DMDM Hydantoin | 0.4 |
| Deionized water | q.s. |

Batch B and the hydroxyethylcellulose are dispersed in water at room temperature with agitation. The mixture is then heated to about 70° C. with stiffing. In a separate container, the glycol distearate, cetearyl alcohol, cetyl alcohol, and the PEG-100 stearate are mixed and heated to about 70° C. Once uniform, the polymer solution is added under stirring, then the stearlkonium chloride, citric acid, and preservative is added, and the conditioner cooled to room temperature with the remaining water added.

Example 7

Exemplary personal care leave-on conditioner compositions of the present invention contain the components recited in TABLE 7 on a weight/weight basis (wt. %).

TABLE 7

|  | Formulation D |
|---|---|
| CELLOSIZE PCG-10 Hydroxyethylcellulose | 0.5 |
| PROMULGEN G Stearyl Alcohol and Ceteareth-20 | 1.5 |
| Batch A (2%) | 5.0 |
| JEECHEM S-13 Stearamidopropyl Dimethylamine | 0.8 |
| LANNETTE 16 Cetyl Alcohol | 2.0 |
| DC 1784 HVF Emulsion Dimethiconol and TEA Dodecylbenzenesulfonate (50%) | 4.0 |
| JEEQUAT SDQ-85 Stearalkonium Chloride | 1.0 |
| Citric Acid (10%) | 1.7 |
| GLYDANT DMDM Hydantoin | 0.4 |
| Deionized water | q.s. |

Batch A and the hydroxyethylcellulose are dispersed in water at room temperature with agitation. The mixture is then heated to about 60° C. with stiffing. Stearamidopropyl dimethylamine and stearalkonium chloride are added and dissolved. The mixture is heated to about 75° C. and cetyl alcohol and stearyl alcohol and ceteareth-20 are added. Once uniform, mixture is cooled below 40° C. and the silicon emulsion, citric acid, and preservative is added. The conditioner is cooled to room temperature with the remaining water added.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A personal care composition, comprising: a tertiary amine substituted hydroxyethylcellulose selected from the group consisting of N,N-diethylaminoethyl hydroxyethylcellulose, N,N-dimethylaminoethyl hydroxyethylcellulose, N,N-diisopropylaminoethyl hydroxyethylcellulose, N,N-dimethylaminopropyl hydroxyethylcellulose, N-ethyl piperidine hydroxyethylcellulose, N-ethyl morpholine hydroxyethylcellulose, N-ethyl pyrrolidine hydroxyethylcellulose, and mixtures thereof; and at least one cosmetically acceptable surfactant, emollient, or cosmetically active agent.

2. The personal care composition of claim 1, wherein the tertiary amine substituted cellulose derivative is present in a range from about 5 wt % to about 40 wt % by weight of the aqueous dispersion.

3. The personal care composition of claim 1, further comprising a silicone, provided that the silicone is not in the aqueous dispersion.

4. The personal care composition of claim 3, wherein the silicone is present in a range from about 0.1 wt % to about 5 wt % by weight of the personal care composition.

5. The personal care composition of claim 1, wherein the surfactant is present and is a detergent surfactant.

6. The personal care composition of claim 1, wherein the surfactant is present and is a nonionic surfactant.

7. The personal care composition of claim 1, wherein the personal care composition is a shampoo, a rinse-off conditioner, a leave-in conditioner, or a body wash.

8. The personal care composition of claim 1, wherein the tertiary amine substituted cellulose derivative is present in a range from about 15 wt % to about 25 wt % by weight of the aqueous dispersion.

9. The personal care composition of claim 4, wherein the silicone is present in a range from about 0.75 wt % to about 3 wt % by weight of the personal care composition.

10. The personal care composition of claim 9, wherein the silicone is present in a range from about 1 wt % to about 2 wt % by weight of the personal care composition.

11. The personal care composition of claim 5, wherein the detergent surfactant is present in a range from about 1 wt % to about 25 wt % by weight of the personal care composition.

12. The personal care composition of claim 11, wherein the detergent surfactant is present in a range from about 5 wt % to about 20 wt % by weight of the personal care composition.

13. The personal care composition of claim 12, wherein the detergent surfactant is present in a range from about 7 wt % to about 18 wt % by weight of the personal care composition.

14. The personal care composition of claim 1, wherein the surfactant is present and is a cationic surfactant.

15. The personal care composition of claim 14, wherein the cationic surfactant is present in a range from about 0.1 wt % to about 10 wt % by weight of the personal care composition.

16. The personal care composition of claim 15, wherein the cationic surfactant is present in a range from about 1 wt % to about 4 wt % by weight of the personal care composition.

17. The personal care composition of claim 1, wherein the tertiary amine substituted hydroxyethylcellulose is N,N-diethylaminoethyl hydroxyethylcellulose.

* * * * *